United States Patent [19]
Campbell et al.

[11] Patent Number: 5,310,524
[45] Date of Patent: May 10, 1994

[54] CATHETER REPROCESSING AND STERILIZING SYSTEM

[75] Inventors: James L. Campbell; Louis C. Cosentino, both of Plymouth, Minn.

[73] Assignee: Minntech Corporation, Minneapolis, Minn.

[21] Appl. No.: 835,729

[22] Filed: Feb. 11, 1992

[51] Int. Cl.⁵ .......................... A61L 2/00; B08B 9/02
[52] U.S. Cl. ........................................ 422/33; 422/28; 422/292; 422/295; 134/22.12; 134/22.18; 134/166 R; 134/166 C; 134/170
[58] Field of Search ................ 422/28, 33, 292, 295; 134/22.12, 22.18, 166 R, 170, 166 C

[56] References Cited

U.S. PATENT DOCUMENTS

| | | | |
|---|---|---|---|
| 4,410,493 | 10/1983 | Kaye | 422/27 |
| 4,721,123 | 1/1988 | Cosentino et al. | 134/57 |
| 4,759,909 | 7/1988 | Joslyn | 422/295 |
| 4,943,414 | 7/1990 | Jacobs et al. | 422/28 |
| 5,122,340 | 6/1992 | Shimamura et al. | 422/28 |

*Primary Examiner*—Robert J. Warden
*Assistant Examiner*—T. A. Trembley
*Attorney, Agent, or Firm*—Barbara A. Wrigley

[57] ABSTRACT

A system for reprocessing and sterilizing a previously used catheter having at least one lumen is disclosed. The catheter is provided with a housing and enclosed within the housing. Heated sterilant is provided to the housing and the catheter. The lumen is tested during the reprocessing and sterilizing cycle for blockages and integrity. If the catheter is of a type having a balloon tip, the balloon is also tested for integrity by inflating and deflating it a plurality of times. The housing is pressurized to a level above the ambient pressure and maintained at such pressure whereby the sterility of the catheter is maintained for up to one week. Further disclosed is an apparatus for selectively coupling used catheters to a source of sterilant. The apparatus includes a housing having a tray for holding the catheter in place during reprocessing, a door for enclosing and locking the catheter within the housing, and a plurality of valves for coupling the housing to a source of sterilant. In addition, the apparatus includes a cap for maintaining the sterility of the catheter during storage.

14 Claims, 8 Drawing Sheets

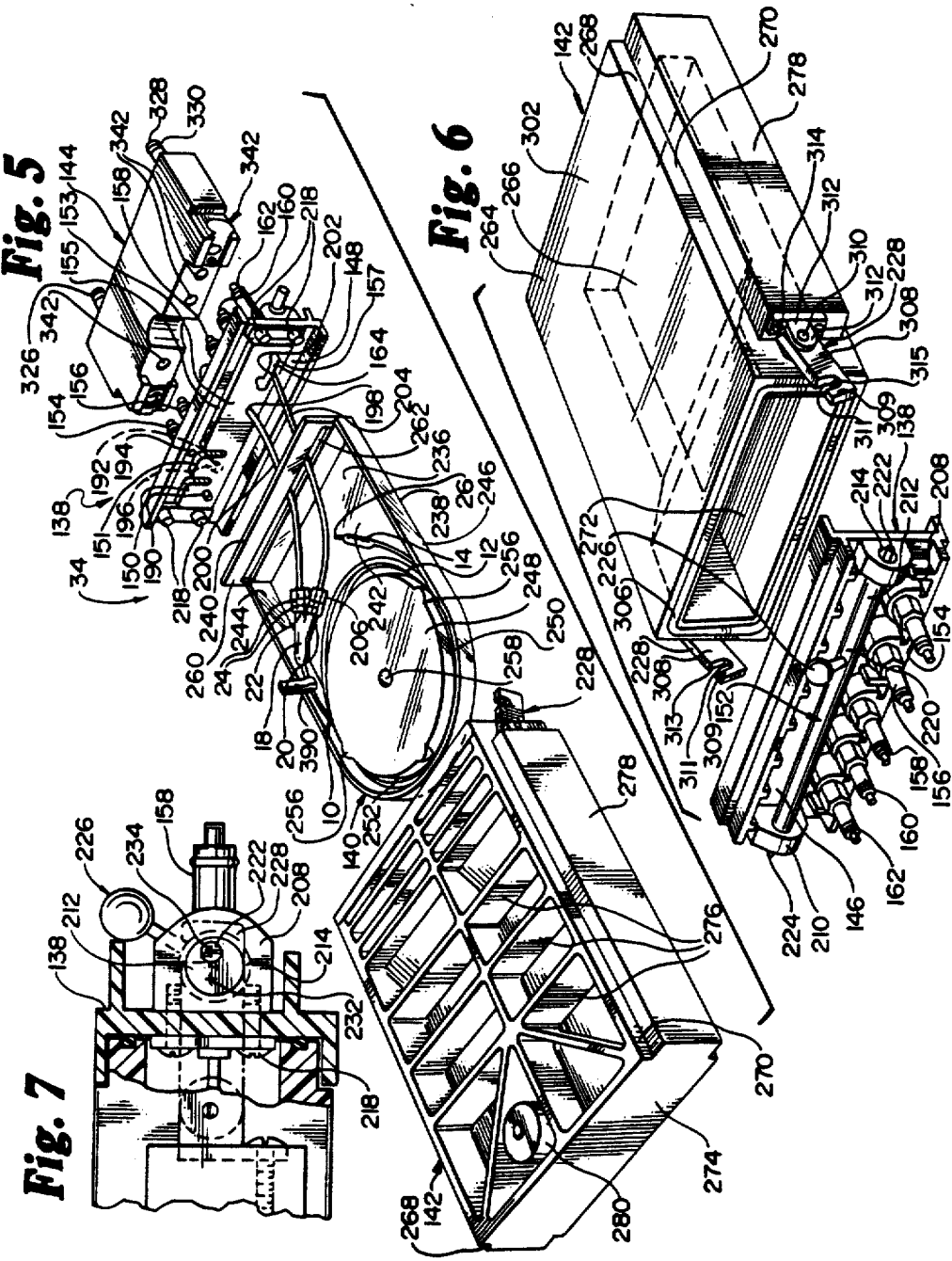

CATHETER REPROCESSING AND STERILIZING SYSTEM

BACKGROUND OF THE INVENTION

1. Field of the Invention

This invention relates generally to the field of reprocessing medical equipment. In particular, it relates to an improved device and method for sterilizing and reprocessing balloon-tipped catheters that are used in the surgical reconstruction of blood vessels.

2. Description of the Related Art

Balloon-tipped catheters were first introduced in the mid-1970's to aid surgeons in performing percutaneous transluminal angioplasty. Percutaneous transluminal angioplasty is one of the recognized methods used to treat arteries that are totally obstructed or partially occluded by plaque. Angioplasty is typically performed by making a puncture wound in the patient's thigh to gain access to the femoral artery. A guidewire is passed through the artery and advanced through the vascular system until the distal end of the wire reaches the arterial stenosis, whether iliac, femoral, femoropopliteal, aortic, renal, splanchnic, coronary or brachiocephalic. A guiding catheter is next advanced over the guidewire until its distal end passes over the distal end of the guidewire. The guidewire is then removed and a special PTA wire is advanced through the guiding catheter up to the locus of the stenotic lesion. The surgeon then manipulates the proximal end of the PTA wire to pass it through the stenotic lesion that is obstructing the artery. Next, a PTA balloon catheter is passed over the PTA wire and positioned adjacent to the stenotic lesion. Thus positioned, the balloon is inflated by injecting thereinto a bio-compatible fluid, such as saline. As the balloon inflates, it contacts and compresses the plaque forming stenotic lesion by urging it radially outward. The plaque is displaced thus restoring patency to the target artery. Once used, the catheter is discarded.

Since balloon-tipped catheters were first introduced during the mid-70's, other types of catheters have been designed for various other types of surgical procedures. For instance, catheters having a balloon tip with a large profile were developed for valvuloplasty procedures. Angiographic catheters with one lumen were developed to diagnose the existence of stenotic lesions in the arteries while guide catheters are used to position other types of catheters within the body.

The number of procedures using different types of catheters increases each year. During 1991 alone the number of procedures worldwide approximated one billion. The cost of the various types of catheters used in these procedures represents a significant portion of the overall cost of the operation. For instance, balloon-tipped catheters used in angioplasty and valvuloplasty procedures cost approximately $600.00/each with the cost increasing each year as variations and improvements are developed. The ability to reprocess and reuse catheters would provide a decided advantage by helping to control the spiraling cost of the surgical procedures utilizing them.

Attempts to develop a system to reprocess catheters have met with limited success. Manual reprocessing of catheters has provided a limited means for reprocessing and reusing the catheters. However, manual reprocessing is prone to human error and the sterility critical to a successful operation cannot be guaranteed. In addition, manual systems cannot guarantee the integrity of the catheter once it is reprocessed. Further, manual systems also fail to provide the necessary identification, monitoring, control and versatility required to produce a safe and efficient catheter reprocessing system.

U.S. Pat. No. 4,721,123 assigned to the same assignee of the present invention describes a method and apparatus for reprocessing catheters that overcomes many of the problems associated with manual reprocessing. However, the catheter sterilizing cassette described therein is costly to manufacture and awkward to use. Further, the reprocessed catheters must be used immediately because it is difficult to maintain pressure within the cassette. Consequently, the sterility of the cassette and the catheter contained therein cannot be maintained for long periods of time during storage. Moreover, the reprocessing cycle takes hours to accomplish because the system is unable to use advanced chemical sterilants that require heating. A new and improved catheter reprocessing and sterilizing system is needed to overcome these problems.

SUMMARY OF THE INVENTION

It is an object of the method and apparatus of the catheter reprocessing and sterilizing system in accordance with the present invention to solve the problems outlined above that have heretofore inhibited the successful and efficient reprocessing of catheters. The method and apparatus of catheter reprocessing and sterilizing in accordance with the present invention provides for the sterilization of catheters in minutes as opposed to hours and enables the use of a unique catheter sterilizing cassette that, as will be shown, permits storage of sterilized catheters for periods of one week to one month without breaks in sterility.

The method of catheter reprocessing and sterilizing in accordance with the present invention includes providing a catheter receiving housing to a previously used catheter, enclosing the catheter within the housing, providing sterilant to said housing and about and within the interior of the catheter, pressurizing the housing to a level above the ambient pressure and maintaining the pressure within the housing at a pressure above the ambient pressure whereby the sterility of the now reprocessed catheter can be maintained for prolonged periods of time exceeding one week.

The unique catheter holding cassette in accordance with the present invention broadly includes catheter housing means having an interior chamber for receiving a catheter to be reprocessed and sterilized, door means for enclosing the catheter within the interior chamber, valve means for introducing a source of sterilant within the chamber and sealing means for maintaining the pressure of the housing means during storage for periods of time exceeding one week.

One of the advantages of the present invention is that the time required for reprocessing used catheters is reduced to minutes as opposed to hours. Another advantage of the present invention is that the storage, over prolonged periods of time exceeding one week, of multiple sterilized catheter containing cassettes is now possible. Perhaps most significantly, the present invention provides the potential for significant cost reductions in surgical proceduresutilizing catheters by making the multiple reuse of catheters more efficient and economically feasible.

These and other objects and advantages of the present invention will become apparent during the course of the following detailed description and appended claims. The invention may best be understood with reference to the accompanying drawings, wherein an illustrative embodiment is shown.

BRIEF DESCRIPTION OF THE DRAWINGS

FIG. 5 is an exploded perspective view of the catheter reprocessing cassette;

FIG. 6 is a perspective detail view of the outer holding canister of the catheter reprocessing cassette taken from the reverse view of FIG. 5;

FIG. 7 is a fragmentary left side elevational view of the catheter reprocessing and sterilizing cassette depicting the locking mechanism of the cassette with parts cut away for clarity;

DETAILED DESCRIPTION OF THE INVENTION

For ease of understanding the preferred embodiment in accordance with the present invention, a typical balloon-tipped catheter will be described. A balloon-tipped catheter has been chosen to exemplify the use of the present invention and is not intended to limit the invention to the reprocessing and sterilizing of balloon-tipped catheters. Rather, the present invention may be utilized with various types of catheters with and without balloon tips such as angiographic or diagnostic catheters, guide catheters, monorail catheters, multiple lumen and single lumen catheters.

Figure 3:
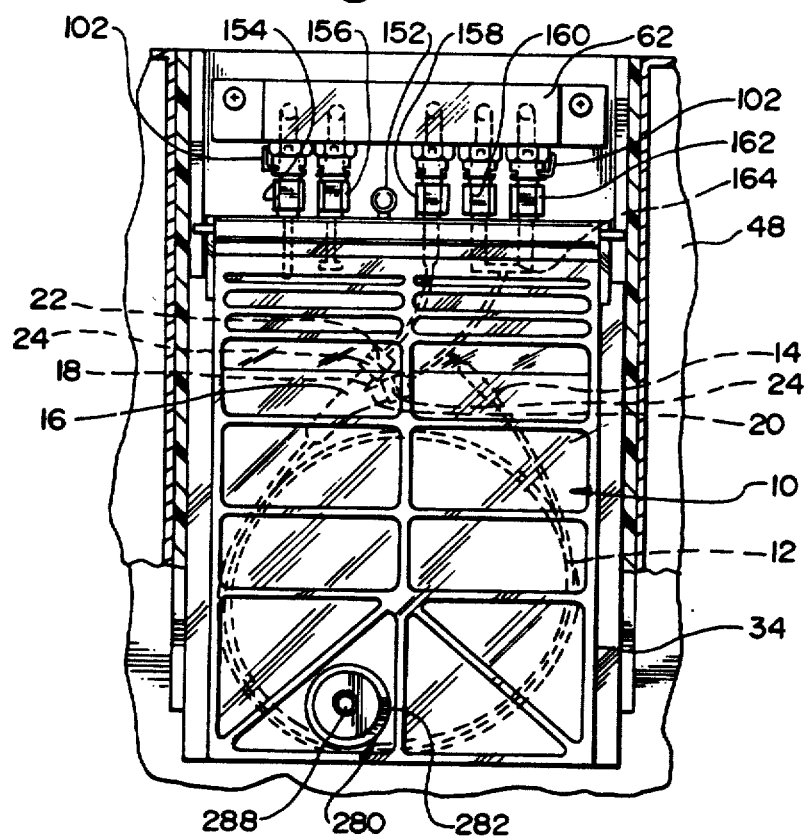
FIG. 3 is a fragmentary top plan view depicting the cassette with parts cut away as mounted on the in the cassette dock.

A typical balloon tipped catheter 10 to be reprocessed and sterilized is shown in phantom lines in FIG. 3 and in FIG. 5. Catheter 10 is generally cylindrical and broadly includes an elongated tubular member 12 and balloon member 14. Tubular member 12 proximal of balloon member 14 includes a central double lumen (not shown) consisting of a balloon inflation lumen (not shown) and a guidewire lumen (not shown). The two lumens are disposed coaxially along tubular member 12 and are separated by a lumen wall (not shown that extends along the longitudinal axis of tubular member 12. The two lumens meet at hub 16.

The bifurcated proximal end 18 of tubular member 12 includes balloon inflation inlet port 20 and guidewire inlet port 22. Inlet ports 20, 22 terminate with standard male luer lock connectors 24. Guidewire inlet port 22 provides the path for introducing a PTA wire through guide wire lumen. Guidewire outlet port 26 located at the distal end of inflation lumen and balloon member 14 opens to air. Balloon inflation inlet port 20 provides the pathway for introducing a bio-compatible sterile solution such as a mixture of saline and contrast media into balloon inflation lumen. Balloon inflation outlet port (not shown), located at the distal end of the balloon inflation lumen, introduces the saline mixture into and inflates the balloon member 14.

Balloon-tipped catheters to be reprocessed are typically 150 cm in length with balloon member 14 being 20 mm in length. The balloon member 14 may withstand pressures of 6 to 17 atmospheres. The ability to withstand such high pressures accounts for the ability of balloon member 14 to compress stenotic lesions formed by plaque and urge the lesions radially outward toward the arterial wall.

During angioplasty procedures or other procedures utilizing catheters, the catheters become contaminated with blood and bodily fluids. Sterilizing the catheter by conventional means such as autoclaving is impractical because the catheter cannot withstand the steam or pressure to which autoclaving subjects it. Similarly, other conventional means, such as gas autoclaving using ethylene oxide or sterilization by gamma radiation, are insufficient because gas autoclaving requires a long cycle time of greater than 24 hours before the catheter is ready for use and sterilization by radiation changes the chemical composition of the material out of which the catheter is made by cross-linking the polymer structure. In addition, however, proteins or antigens adhere to the interior and exterior surface walls of the catheter which conventional means are incapable of dissolving. If the catheter is then reused without adequate sterilization, the antigens may cause a life-threatening reaction in a subsequent patient user. Thus, once used, the catheter must be properly reprocessed and sterilized or discarded.

Figure 1:
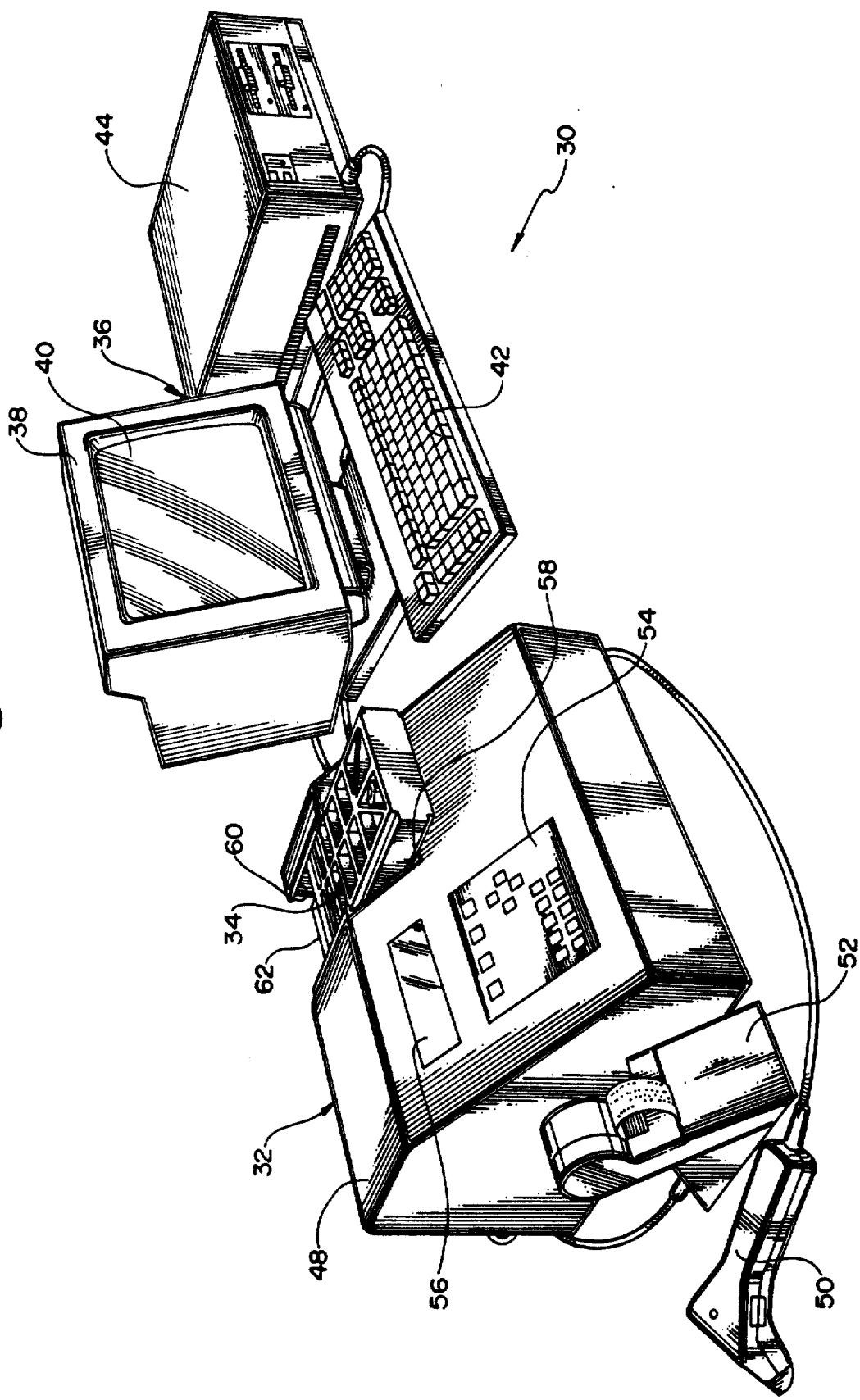
FIG. 1 is a perspective view of the catheter reprocessing and sterilizing system in accordance with the present invention.

Referring to FIG. 1, the catheter reprocessing and sterilizing system 30 in accordance with the present invention broadly includes microprocessor-controlled reprocessing and sterilizing unit 32, catheter sterilizing cassette 34 and computer system 36.

Computer system 36 includes monitor 38 with screen 40, keyboard 42, CPU 44 and printer (not shown). The computer system may be purchased from any commercial compute manufacturer. The preferred embodiment 36 depicts a Northgate 286 computer with two megabytes of ram and 60 megabytes of hard drive storage space available from Northgate Computer Systems, Inc. (Minneapolis, Minn.). Keyboard 42 is a standard typewriter-type keyboard such as the OmniKey 102 also available from Northgate Computer Systems, Inc. The computer 36 is used for the storage and display of data that is generated during the course of reprocessing. The printer (not shown) is used to print out data related to manufacturer, number of time reprocessed, etc. stored by computer and may be any Epson-compatible model. The preferred embodiment makes use of a Panasonic 24 PIN MultiMode printer KX-P1124 available from Matsushita Electric Industrial Company (Tokyo, Japan).

Microprocessor-controlled reprocessing and sterilizing unit 32 includes housing 48, bar code scanner 50, and label printer 52. Housing 48 includes control 54 and display 56 panels, cassette dock 58 with side track mounts 60 and manifold 62. Housing 48 covers hydraulic system 49.

Figure 2A:
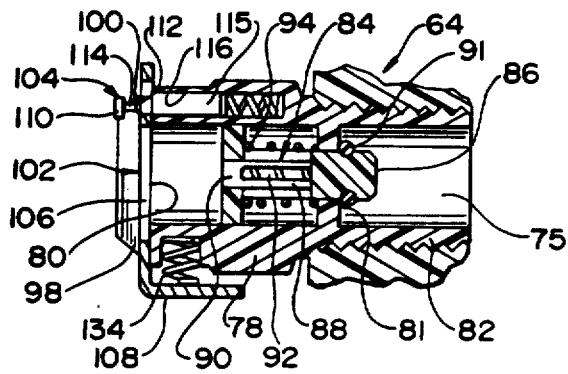
FIG. 2A is a fragmentary detail view depicting an open receptacle valve shown cut vertically along the longitudinal axis.
Figure 2B:
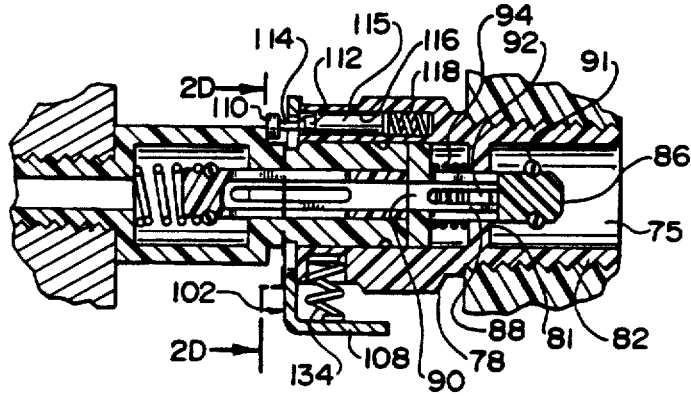
FIG. 2B is a fragmentary detail view depicting the receptacle and projection valves in mating assembly.
Figure 2C:
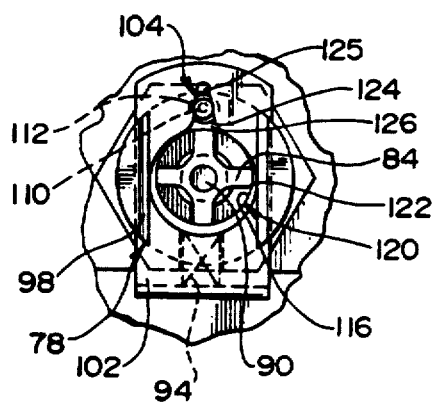
FIG. 2C is a fragmentary detail view into the mouth of the receptacle valve shown in FIGS. 2A and 2B.
Figure 2D:
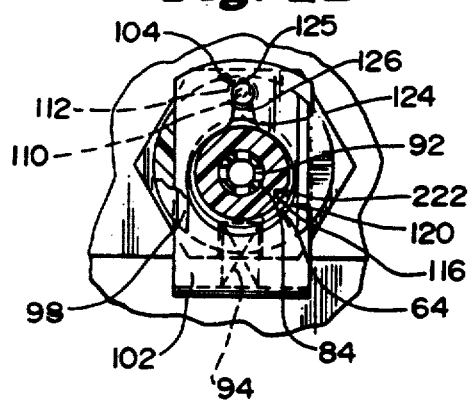
FIG. 2D is a fragmentary detail view taken along line 2D—2D in FIG. 2B.
Figure 2:
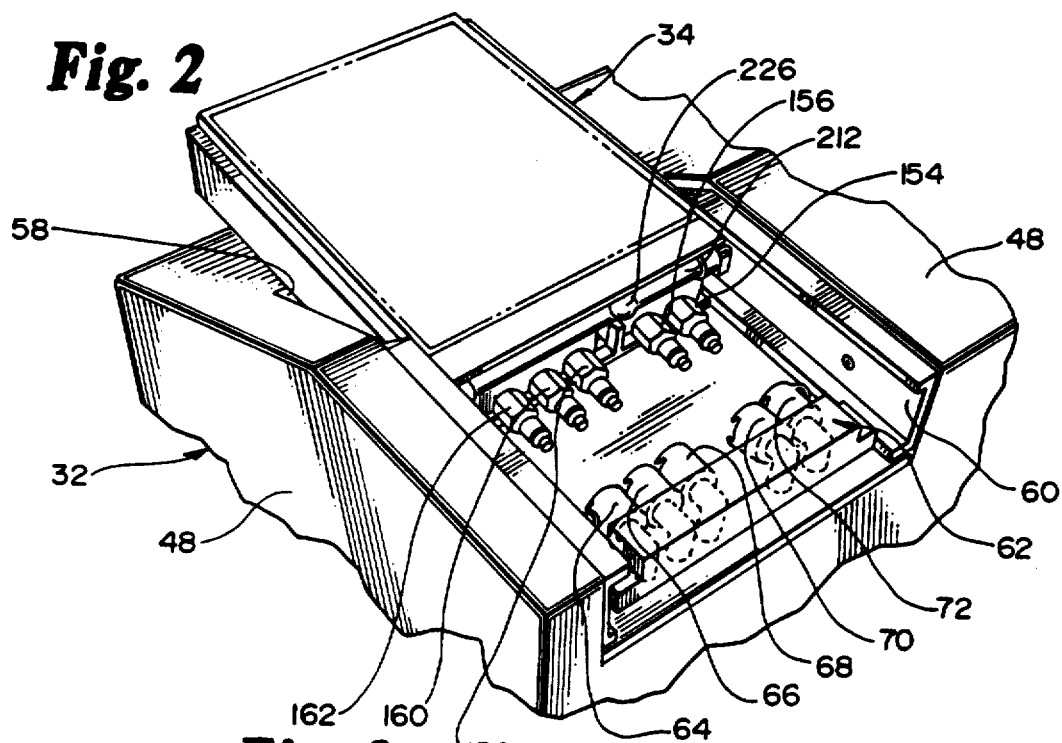
FIG. 2 is a fragmentary perspective view depicting the catheter reprocessing cassette in accordance with the present invention shown mounted in the cassette dock.
Figure 11:
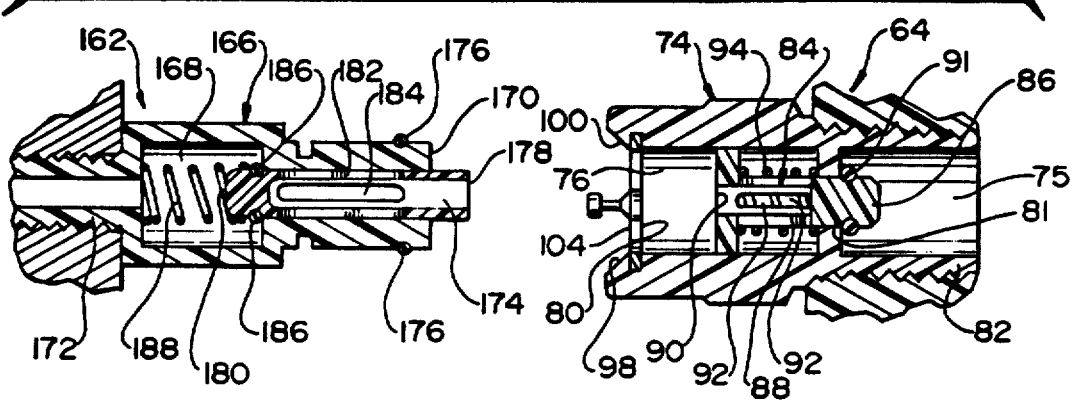
FIG. 11 is a side sectional view of a valve assembly showing valves disconnected.
Figure 12:
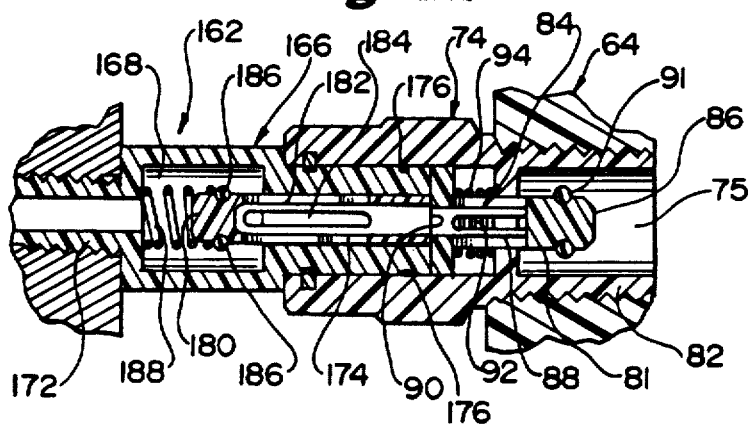
FIG. 12 is a side sectional view thereof showing valves connected.

As may be seen in FIG. 2, manifold 62 rests in housing 48 and includes a plurality of female valve receptacles 64, 66, 68, 70, 72 each having a sterilant transmitting conduit 75. Referring in particular to FIGS. 11 and 12, valve receptacles 64–72 include receptacle connection 74 defining a sterilant receiving conduit 76, body 78, mouth 80, exit port 81, threaded end 82 and retractable receptacle plunger 84. Valve receptacles 64–72 are detachably coupled to manifold 62 by threaded ends 82 allowing an operator to replace them in cases of wear or malfunction.

Referring to FIGS. 11 and 12, receptacle plunger 84 includes head 86, plunger body 88 and perforated disklike orifice 90. Sealing O-ring 91 is carried by head 86. Plunger body 88 includes slotted ports 92 and rests within sterilant-receiving conduit 76. Plunger body 88 carries compression spring 94 which biases plunger 84 is in a closed position when not connected to cassette 34 as depicted in FIG. 11. O-ring 91 seals head 86 against exit port 81 in an air-tight relationship when plunger 84 is in the closed position, preventing fluid from entering sterilant-receiving conduit 76 from sterilant transmitting conduit 75.

Referring to FIG. 2A, valve receptacle mouth 80 includes opposed fastener top plate grooves 98, 100 and fastener 102. Fastener top plate grooves 98, 100 are located at the periphery of mouth 80 but do not extend around the entire circumference of mouth 80.

Fastener 102 includes reciprocating pin 104, top plate 106 and finger-pushable tab 108. Reciprocating pin 104 includes upper and lower pin heads 110, 112, neck 114 and shank 115. Upper and lower pin heads 110, 112 have the same outer diameter, which diameter is larger than the outer diameter of neck 114. Upper pin head 110 has an outer diameter larger than the inner diameter of pin receiving bore 116. Neck 114 and lower pin head 112 have outer diameters that are less than the inner diameter of pin receiving bore 116. Shank 115 has a diameter slightly less than the inner diameter of bore 116 allowing it to be shiftably received in pin receiving bore 116. In the unlocked position, shank 115 is biased upwardly by compression spring 118.

Top plate 106 defines a key-shaped aperture 120 as depicted in FIGS. 2C and 2D including a generally circular key-head shaped aperture 122 adjoining a tapered notch 124 having first and second ends 126, 125. The circumference of key-head aperture 122 is slightly larger than the circumference of receptacle mouth 80. The inner diameter of first end 126 is slightly smaller than the outer diameter of lower pin head 112, preventing pin 104 from exiting pin receiving bore 116 while in the unlocked position as depicted in FIGS. 2A and 2C. The inner diameter of second end 125 is smaller than the outer diameter of upper pin head 110 preventing pin 104 from receding into pin body-receiving bore 116 in the locked position as shown in FIG. 2B and 2D. Neck 114 has an outer diameter less than the inner diameters of both first end 126 and second end 125 allowing pin 104 to reciprocate between the locked and unlocked positions as depicted in FIGS. 2B and 2A, respectively.

Finger-pushable tab 108 is generally oval in shape and extends outwardly and downwardly at a 90° angle from top plate 106. Tab 108 is positioned adjacent to body 78 of valve receptacles 64–72. Compression spring 134 is received within bore 136 and biases tab 108 outwardly. In the unlocked position as shown in FIGS. 2A and 2C, spring 134 is compressed and tab 108 rests substantially flush against valve receptacle body 78; pin 104 is biased outwardly and first end 126 of tapered notch 124 stops lower pin head 112 from passing through thus preventing pin 104 from exiting bore 116. In the locked position as shown in FIGS. 2B and 2D, tab 108 is biased outwardly by spring 134 and pin 104 retracts as it contacts the surface of valves 154–162.

Referring to FIG. 1, bar code scanners 50 are well known for electronically reading "bar codes" that are encoded on merchandise or units of items to signify manufacturer information, unit price, etc. In the preferred embodiment, the bar code scanner 50 is a Scan Team 5880 available from Welch Allyn (Skaneateles, N.Y.). Label printers 52 are also well known in the art and are commercially available from sources such as computer manufacturers. The printer depicted in the preferred embodiment is a Seiko SLP-1000 and is available from Seiko Instruments Inc. (San Jose, Calif.).

Referring to FIGS. 5 and 6, the reprocessing and sterilizing cassette 34 in accordance with the present invention broadly includes cassette door 138, disposable tray 140, canister 142 and cap 144.

Cassette door 138 or door means is generally rectangular in shape and includes front panel 146, back panel 148 and locking mechanism 152. Front and back panels 146, 148 supports generally cylindrically-shaped valve means or recirculating fill and drain valve 154, overflow valve 156, guidewire lumen fill and drain valve 158, and balloon inflation lumen fill and drain valves 160, 162. Balloon inflation lumen fill and drain valves 160, 162 are maintained in fluid communication by U-shaped connecting channel 164.

Back panel 148 includes tray mount tabs 150, 151, 153 and upper and lower edges 155, 157.

Referring again to FIGS. 11 and 12, valves 154, 156, 158, 160, 162 include valve body 166 with central duct 168, valve mouth end 170, threaded connecting end 172, and retractable valve plunger 174. Mouth end 170 carries O-ring 176 on its external surface. Plunger 174 is retractably received within central duct 168 and includes first and second ends 178, 180 and body 182 with slotted channel 184. Second end 180 carries O-ring 186 and engages compression spring 188. Spring 188 biases plunger 174 in a closed position as depicted in FIG. 11. O-ring 176 seals mouth end 170 in an air-tight relationship when plunger 174 is closed preventing fluid from entering central duct 168 via mouth end 170. When inserted into valve receptacle 64 as shown in FIG. 12, first valve plunger end 178 contacts disk-like orifice 90 of receptacle plunger 84, such that receptacle plunger 84 and valve plunger 174 slidably retract putting central duct 168 and sterilant-receiving conduit 76 in fluid communication with each other.

Threaded connecting end 172 of valves 154, 156, 158 160, 162 is detachably embedded within front and back panels 146, 148 of cassette door 138. Referring again to FIGS. 5 and 6, central duct 168 of recirculating fill and drain valve 154 terminates in jet aperture 190 located at the lower edge 157 of back panel 148. Jet aperture 190 is approximately 0.012–0.020 inches in diameter and most preferably is 0.016 inches in diameter. During reprocessing, sterilant is pumped through jet aperture 190 at a rate of 0.5 L/min creating a high velocity fluid stream circulating and recirculating through cassette 34.

Overflow valve 156 terminates in overflow vent 192 located along the lower edge 157 of back panel 148. Vent 192 and vent outlet 194, which opens to air, are fluidly connected by fluid-flow passage 196. Guidewire lumen fill and drain valve 158 terminates in outlet 198. Line 200 with female luer lock connector 206 runs from outlet 198 and is in fluid communication with guidewire lumen inlet port 22. Balloon inflation fill and drain valves 160, 162 are connected by U-shaped channel 164 which terminates in outlet port 202. Line 204 with female leur lock connector 26 runs from outlet port 202 and is in fluid communication with balloon inflation lumen inlet port 20.

Referring to FIGS. 6 and 7, overcenter cam locking means 152 consists of journals 208, 210 and cam shaft 212. Journals 208 210 are generally C-shaped in cross section and define peg receiving apertures 214, 216. Journals 208, 210 are fixedly mounted on cassette door 138 by rivets 218, screws or the like.

Cam shaft 212 includes a generally cylindrical rod 220, first and second cam pegs 222, 224 and cam lever and knob assembly 226. First and second cam pegs 222, 224 are rotatably received within peg receiving apertures 214, 216, respectively. As cam shaft 212 is rotated upwardly toward door 138 by shifting cam lever and knob assembly 226 upwardly, cam pegs 222, 224 also move upwardly, engagably coupling lock latches 228. Over-center locking mechanism 152 locks when the central axis of lever 230 passes across a line extending through the central rotational axis of shaft 232 and pegs 234. In the locked position, cam shaft 212 rests against and lends support to door 138, preventing door 138 from moving outwardly as pressure is applied to the interior of cassette 34.

Referring to FIG. 5, disposable tray 140 is a unitary, U-shaped piece and includes generally planar top and bottom surfaces 236, 238 and connecting flap 240. Tray 140 is preferably transparent and is molded from any flexible, resilient, synthetic resin material such as polyvinylchloride, polyolefin or other suitable materials.

Top surface 236 includes integrally molded recessed portion 242, U-shaped internal and external sidewalls 244, 246, and circular projection 248 with outer side wall 250. Internal sidewall 244 defines recessed portion 242 which acts as a sterilant solution receiving cavity. Internal side wall 244 of tray 140 and outer side wall 250 of circular projection 248 define a catheter holding groove 252. Outer sided wall 250 and internal side wall 244 support a plurality of molded C-shaped stop flanges 256 which act as pinch points to maintain catheter 10 securely in place during reprocessing.

Circular projection 248 includes sterilant circulating aperture 258 providing for reprocessing sterilant to access all areas of tray 140.

Generally planar bottom surface 238 includes a plurality of support ribs (not shown) that give strength to tray 140 and support tray during the reprocessing process.

Connecting flap 240 includes elongated interface 260 defining pass-through slit 262. Pass-through slit 262 is located along the horizontal axis of flap 240 and allows lines 200, 204 and leur lock connectors 206 to be threaded through slit 262 and be operably coupled to female leur lock connectors 24. Balloon inflation lumen ill and drain valves 160, 162 and guidewire lumen fill and drain valve 158 are thus in fluid communication with balloon inflation lumen inlet port 20 and guidewire lumen inlet port 22, respectively. Elongated interface 260 is positioned over tray mount tabs 150, 151, 153 located on the back panel 148 of door 138 and holds tray 140 horizontally secure during reprocessing.

Referring to FIGS. 5 and 6, canister 142 includes upper and lower outer surfaces 264, 266, left and right opposed side walls 268, 270, back wall 274, opposed mouth 272 and lock latches 228.

Canister 142, or housing means, is an integrally molded unitary piece which is generally rectangular in cross section. Canister 142 is molded from any synthetic resin material which is sufficiently rigid and strong upon curing such as polycarbonate, polyester or other suitable materials. Strength ribs 276 are integrally molded with upper and lower outer surfaces 264, 266 and provide support to canister 142. Side walls 268, 270 of canister 142 support rectangular in cross section side tracks 278. As best seen in FIG. 2, side tracks 278 engagably couple side track mounts 60 on housing 48 as cassette 34 is coupled to manifold 62 during reprocessing.

Figure 13:
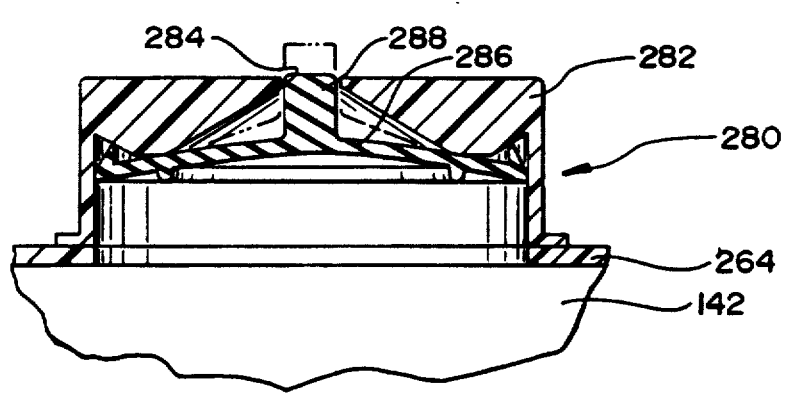
FIG. 13 is a fragmentary side elevational sectional view depicting the pressure monitor as it is disposed within the cassette.

Referring to FIG. 13, pressure monitor 280, or sterility monitoring means, is carried by upper surface 264. Pressure monitor 280 includes outer casing 282 defining a casing aperture 284 and elastomeric finger actuated diaphragm signal device 286 carried within the casing 282. Diaphram 286 includes a finger engageable button 288 protruding from the center of diaphram 286. Diaphram is preferably made from ethylene propylene diene monomer, or other similar materials. Pressure is sensed by pressing the button 288 extending through the aperture 284 in casing 282 and manually determining the resistance provided thereto. The pressurized profile of monitor 280 is depicted in phantom lines with button 288 protruding from casing 282.

Referring again to FIGS. 5 and 6, mouth 272 provides access to tray-receiving compartment 302 defined by upper and lower surfaces 264, 266, right and left side walls 268, 270 and back wall 274. Recessed groove 304 extends around the perimeter of mouth 272 274. O-ring 306 sits in recessed groove 304, around the perimeter of mouth 272 and contacts the perimeter of back panel 148 of cassette door 138 in a sealing relationship when tray 140 mounted on door 138 is inserted into mouth 272. As an operator rotates cam lever and knob assembly 226 to its locking position, the engagement of the door 138 with O-ring 306 compresses the O-ring 306 against the back panel 148 providing an air tight seal between door 138 and tray-receiving compartment 302.

Referring to FIG. 6, lock latches 228, or latch means, include latch arms 308, pivot pins 310 and latch mounts 312. Latch mounts 312 are embedded within and fixedly connected to side tracks 278 by rivets, screws or other suitable means 314. Latch arms 308 include single hook 309 defining notch 311. Notch 311 includes top and bottom recessed portions 313, 315. In an alternative embodiment, latch arms 308 may include double notches (not shown).

Latch arms 308 are pivotally connected to latch mounts 312 by pivot pins 310. Pivot pins 310 allow latch arms 308 to rotate freely and engagably couple cam pegs 222, 224 with the top recessed portion 313 of notch 311 thus providing the means for fastening cassette door 138 to canister 142.

Figure 9:
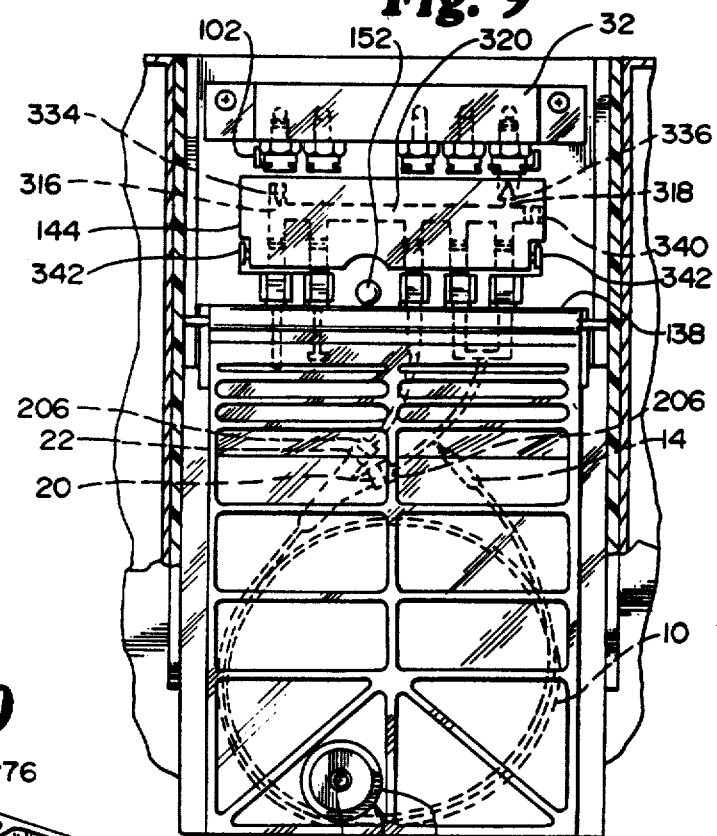
FIG. 9 is a fragmentary top plan view of the reprocessing and sterilizing cassette in accordance with the present invention with parts cut away, with a catheter carried by the cassette depicted in phantom lines.
Figure 10:
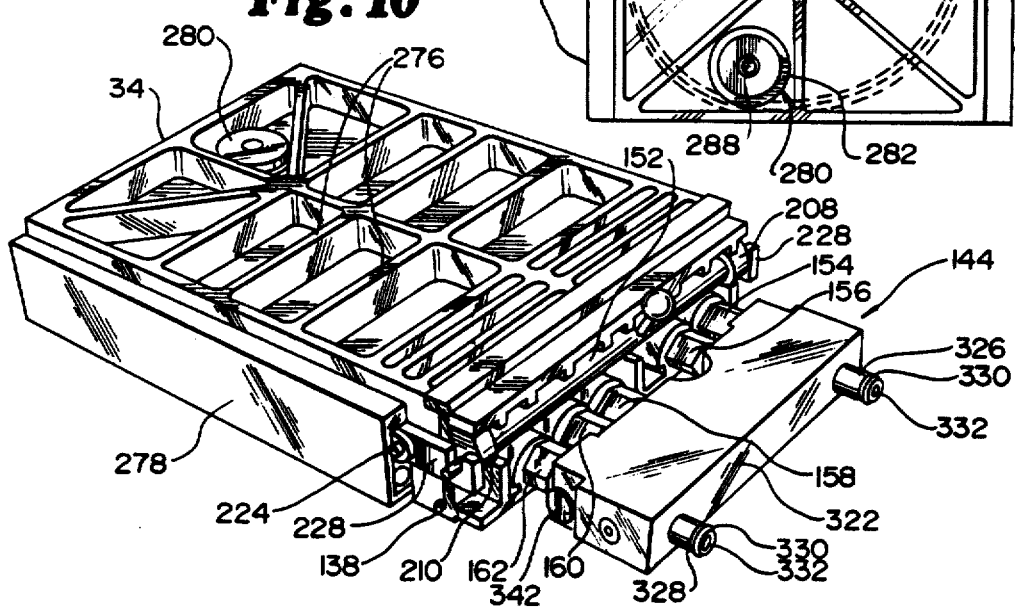
FIG. 10 is a perspective view of the catheter reprocessing cassette ready for storage.
Figure 9A:
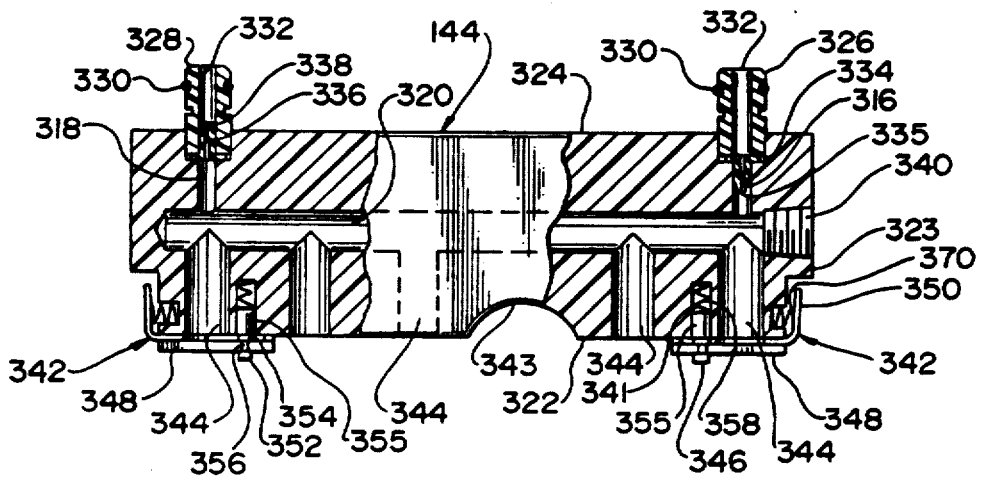
FIG. 9A is a top plan view depicting the cap with locking mechanism in open position with parts cut away.
Figure 9B:
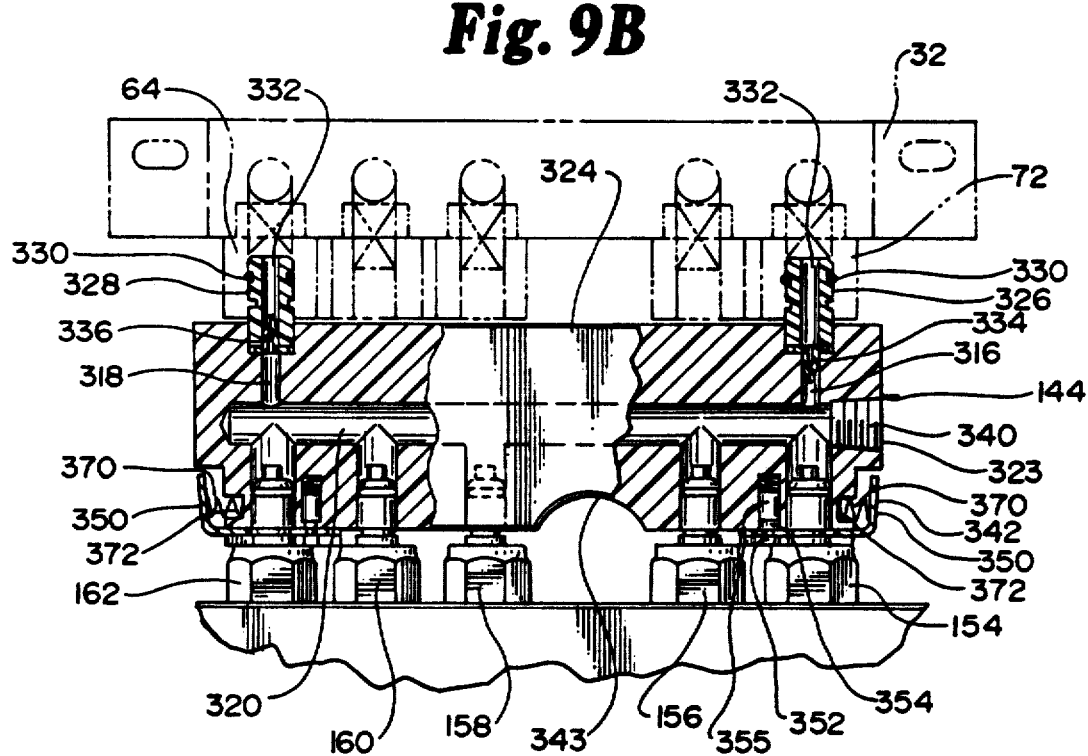
FIG. 9B is a top plan view depicting the cap positioned on the valve assembly of the cassette as it is docked during reprocessing.

As best seen in FIGS. 9A and 9B, cap 144, or sterility maintaining cap means, includes first and second fluid-flow channels 316, 318, interior chamber 320, front and back faces 322, 324 and side panels 323, 325.

Back face 324 of cap 144 includes purge-in 326 and purge-out 328 ports supporting O-ring seals 330 at mouth inlet 332. Mouth inlet 332 of purge-in and purge-out ports 326, 328 provide fluid flow communication with first and second fluid-flow channels 316, 318. Channels 316, 318 extend along the vertical axis of cap 144 and include first and second duck-bill valves 334, 336 therewithin. First duck-bill valve 334 is positioned within first fluid-flow channel 316 with duck bill flap 335 oriented downwardly toward front face 322. Second duck-bill valve 336 is positioned within second fluid-flow channel 318 with duck bill flap 338 oriented upwardly toward back face 324.

Interior chamber 320 extends along the length of cap 144 and provides a pathway for fluid communication between fluid-flow channels 316, 318. Plate 340 provides access to interior chamber 320 to allow the operator to clean the interior channels 316, 318, remove foreign debris from chamber 320, service duck bill valves 334, 336 or like functions.

Front face 322 of cap 144 includes pin-receiving bore 341, at least one fastener 342, indentation 343 and a plurality of valve receiving pockets 344 into which valves 154, 156, 158, 160 are accepted.

Fastener 342 includes reciprocating pin 346, top plate 348 and finger-pushable tab 350. Reciprocating pin 346 includes upper and lower pin heads 352, 354, neck 356 and shank 355. Upper and lower pin heads 352, 354 have the same outer diameter, which is larger than the outer diameter of neck 356. Upper pin head 352 has an outer diameter larger than the inner diameter of pin-receiving bore 341. Neck 356 and lower pin head 354 have outer diameters less than the inner diameter of the pin-receiving bore 341. Shank 355 has a diameter slightly less than the inner diameter of bore 341 allowing it to be shiftably received in pin-receiving bore 341. Shank 355 is biased upwardly by compression spring 358 in the unlocked position as best seen in FIG. 9A.

The details of top plate 348 of fastener 142 is not shown in FIGS. 9A or 9B but is the same as the top plate configuration depicted in FIGS. 2C and 2D.

Finger-pushable tab 350 is generally oval in shape and extends downwardly at a 90° angle from top plate 348. Tab 350 is positioned adjacent to side panels 323, 325 of cap 144. Compression spring 370 is received within bore 372 and biases tab 350 outwardly. In the open position as seen in FIG. 9A, spring 370 is compressed and tab 350 rests substantially flush against notched side panel 323 and pin 346 is biased outwardly by spring 358. In the locked position as seen in FIG. 9B, tab 350 is biased outwardly by spring 370 and upper pin head 352 retracts as it contacts the surface of valve 154.

Figure 4:
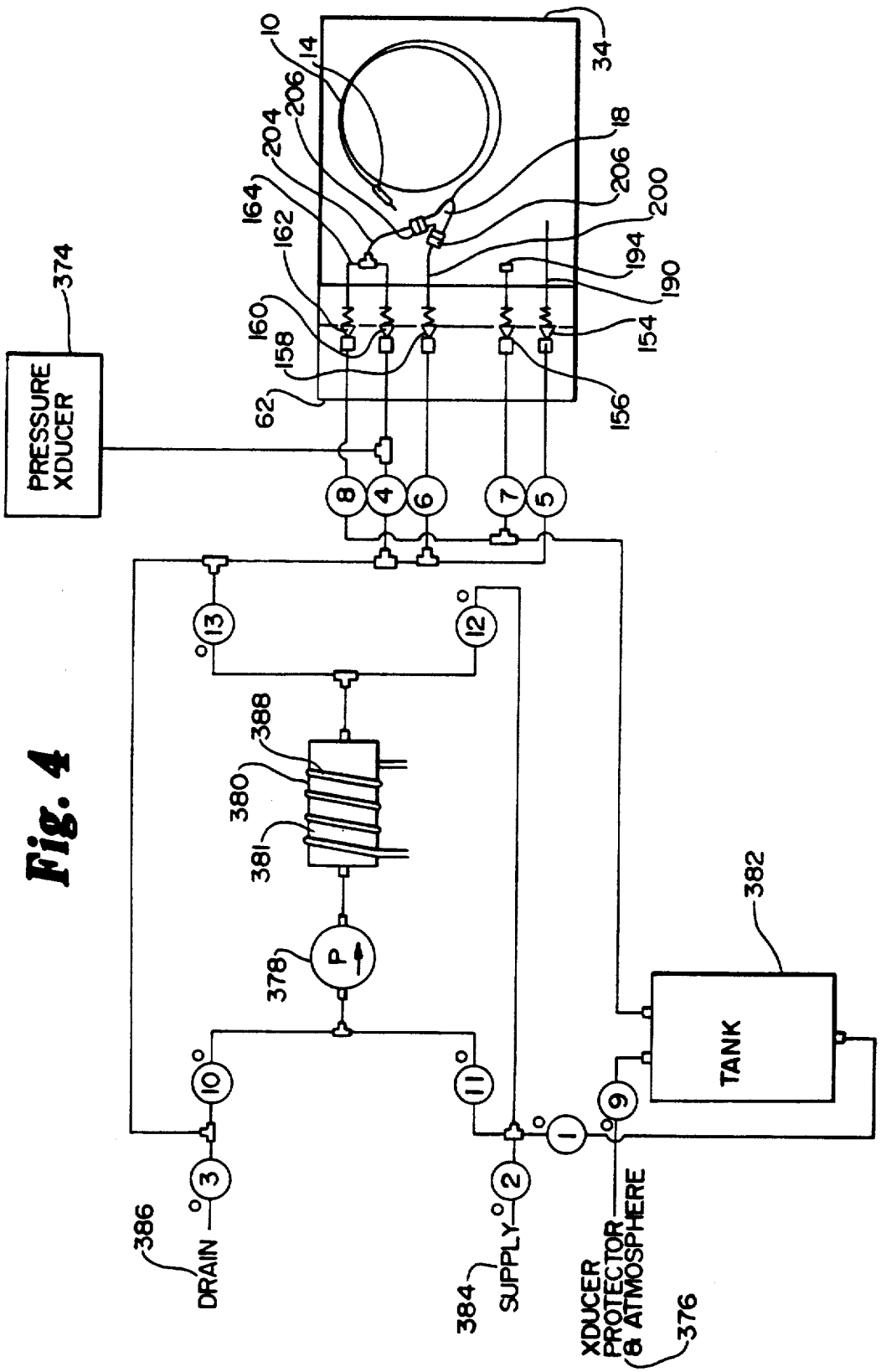
FIG. 4 is a schematic diagram of the hydraulic mechanism of the catheter reprocessing and sterilizing system.

Referring to FIG. 4, the hydraulic system 49 includes thirteen normally closed solenoid valves annotated as V1-V13, pressure transducer 374, air filter 376, pump 378, heater 380, tank 382, sterilant supply 384 and sterilant drain tank 386.

Pressure transducer 374 is well known in the art and any suitable variety capable of accurate measurements to 500 psi such as the MediaMate 930-2906 available from Data Instruments Inc. (Acton, Mass.) is adequate.

Air filters 376 are also know in the art. Filters capable of filtering contaminants 0.22 um in size such as the Millex-GS, 0.22 um filter unit available from Millipore Products Division (Bedford, Mass.) are adequate. Filter 376 protects the transducer 374, hydraulic system 49 and manifold 62 from atmospheric contaminants such as viruses and bacteria.

Pump 378 is well known in the art and any suitable positive displacement gear pump capable of pressures of at least 300 psi such as the Micropump 200-062 available from Micropump, Inc. (Concord, Calif.) will suffice.

Heater 380 is a solid cylindrically-shaped aluminum block 381 with grooves (not shown) cut circumferentially in a helical fashion and includes two resistive heating elements (not shown). Hollow coil 388 is wound in a helical fashion around block 381. Sterilant passes through hollow coil 388 and is heated by heater 380 before it is utilized in sterilizing catheter 10. The size and cubic volume of aluminum block 381 is calculated to heat sterilant to the preferred initial temperature of 37° C. during the Load Sterilant step described below.

A microprocessor (not shown) monitors the output signal of pressure transducer 374, controls the opening and closing of solenoid valves V1-V13, pump 378, and the temperature of heater 380. The valves V1-V13, pump 378 and heater 380 are disposed in a number of different configurations to complete the steps described below that are necessary to reprocess and test catheter 10. Table I below indicates the various steps involved in the reprocessing and sterilizing process and the corresponding states of the valves V1-V13, pump 378 and heater 380.

Referring to Table I, an X indicates that a valve is open or active. An H means that the heater 380 is in standby mode and is maintaining the temperature of aluminum block 381 constant. S1 indicates that the heater circuit is receiving feedback from the temperature of the sterilant and maintains it at a constant 38° C. An S2 indicates that the heater circuit is receiving feedback from the sterilant being circulated throughout the system and maintains it at a constant 53° C.

TABLE I

|  | V1 | V2 | V3 | V4 | V5 | V6 | V7 | V8 | V9 | V1 | V1 | V1 | V1 | P | H |
|---|---|---|---|---|---|---|---|---|---|---|---|---|---|---|---|
| Waiting for use |  |  |  |  |  |  |  |  | X |  |  |  |  |  | H |
| Load Sterilant |  | X |  | X | X | X | X |  |  |  | X |  | X | X | S1 |
| Circulate Sterilant 38C | X |  |  | X | X | X | X |  |  |  | X |  | X | X | S1 |
| Test lumen (step 1) | X |  |  | X |  | X | X |  |  |  | X |  | X | X |  |
| Test lumen (step 2) |  |  | X | X | X |  |  |  |  |  |  |  |  |  |  |
| Test lumen (step 3) | MONITOR PRESSURE FOR 5 SECONDS | | | | | | | | | | | | | | |

TABLE I-continued

|  | V1 | V2 | V3 | V4 | V5 | V6 | V7 | V8 | V9 | V1 | V1 | V1 | P | H |
|---|---|---|---|---|---|---|---|---|---|---|---|---|---|---|
| Test balloon (step 1) | X |  | X |  |  |  |  |  |  | X |  | X | X |  |
| Test balloon (step 2) | MONITOR PRESSURE FOR 5 SECONDS | | | | | | | | | | | | | |
| Circulate Sterilant 50C | X |  | X | X | X | X |  |  |  | X |  | X | X | S2 |
| Clear balloon line | X |  | X |  |  |  | X | X |  | X |  | X | X |  |
| Inflate balloon | X |  | X |  |  | X |  |  |  | X |  | X | X |  |
| Deflate balloon | X |  | X |  |  | X |  |  | X |  | X |  | X |  |
| Check system pressure |  |  |  | X | X | X | X | X |  |  |  |  |  |  |
| Vent system pressure |  |  |  | X | X | X | X |  | X |  |  |  |  |  |
| Fill cap | X |  |  | X | X |  |  | X |  |  | X |  | X | X |
| Drain tank | X | X |  | X |  |  |  |  |  |  | X |  | X | X |
| Cassette to tank | X |  |  |  | X |  | X |  | X | X |  | X |  | X |

Figure 8:
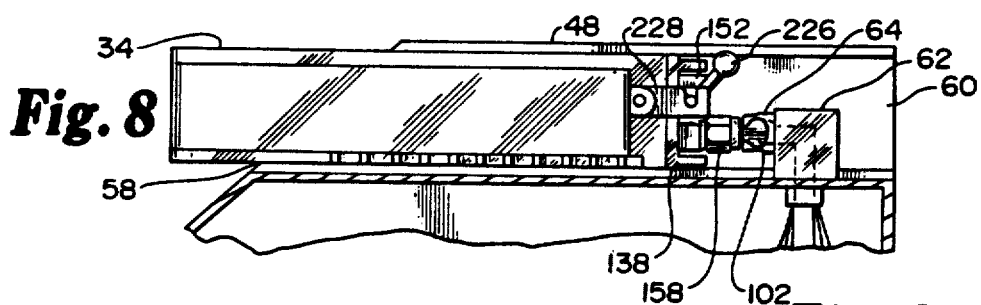
FIG. 8 is a fragmentary left side elevational view depicting the catheter reprocessing cassette as it is docked during an exemplary reprocessing procedure.

In operation, a typical reprocessing and sterilizing cycle will consist of the above-referenced processes executed in an order that will sterilize and test catheter 10. Referring to FIGS. 2, 8 and 9, catheter 10 is wound around projection 248 of tray 140 and pressed into catheter holding groove 252. Stop flanges 256 hold catheter 10 securely in place. The operator turns on the catheter reprocessing and sterilizing machine and scans bar code tag 390 with bar code scanner 50. The screen will display a signal that it recognizes the catheter as having been reprocessed before or will ask the operator to add relevant manufacturer data.

Guidewire lumen inlet port 22 terminating in female leur lock connector 24 is connected to male leur lock 206. Male leur lock 206 is connected by line 200 to guidewire lumen fill and drain valve 158. Balloon inflation inlet port 20, terminating in female leur lock connector 24 is connected to male leur lock 206. Male leur lock 206 is connected by line 204 to balloon inflation lumen fill and drain valves 160, 162. The operator turns on the catheter reprocessing and sterilizing unit and scans the bar code tag 390 on catheter 10. The microprocessor automatically verifies that the computer is operationally coupled with the reprocessing system and then displays the main menu. The computer displays a prompt that the bar code has been received. A prompt signals the operator to press "enter" to start the reprocessing cycle, press "failure" to visually fail the catheter, or quit if the operator decides not to reprocess the catheter.

The operator then places cassette door 138 onto canister 142. Latch arms 308 are coupled to cam pegs 222, 224. Cam lever and knob assembly 226 is rotated upwardly and cassette door 138 compresses O-ring 306 in sealing engagement and is locked as cam pegs 222, 224 rotate into a locked position against the top recessed portion 313 of notch 311.

Referring to FIG. 8, cassette 34 is manually loaded into cassette dock 58. Side tracks 278 engagably couple track mounts 60 and prevent cassette 34 from being displaced during reprocessing. Male valves 154, 156, 158, 160, 162 couple with female valve receptacles 64, 66, 68, 70, 72 resting on housing 48 and valve receptacle fasteners 102 lock cassette 34 into place. The operator then presses "enter" to start the reprocessing cycle.

Referring to FIG. 4, the microprocessor controls the sequencing of solenoid valves, pump and heater in the following manner:

1. Load Sterilant—Part A. Valves V2, V4, V5, V6, V7, V11 and V13 are open. Sterilant is pumped from the supply tank 384 to the cassette 34 through valves V2, V11, through heater 380, through V13, through V6 into the guidewire lumen (not shown) and the guidewire lumen fill and drain valve 158 and guidewire lumen inlet port 22. Sterilant flows through guidewire lumen (not shown) and exits through guidewire lumen outlet port 26 into cassette 34. Sterilant also flows from V13 through V5 into central duct 168 of recirculating fill and drain valve 154 and exits through jet aperture 190 into the interior of cassette 34. When cassette 34 is full, the excess sterilant flows out through overflow vent outlet 194, overflow vent 192, overflow valve 156, valve V7 and into tank 382. However, the cassette 34 remains full with sterilant. Valve V4 is open to provide monitoring of the pressure within the manifold 62 by transducer 374.

Every 30 seconds during the Load Sterilant step, the microprocessor checks the pressure of the system. To check system pressure, valves V4, V5, V6, V7 and V8 are open. Valve V7 is open to equalize pressure between the interior of the cassette and tank 382. The microprocessor reads the pressure from transducer 374. If the pressure is greater than 8 psi, pressure is vented from the system until a pressure of 6 psi is reached. Pressure is vented by opening valves V4, V5, V6, V7, and V9. The acid sterilant used during the reprocessing and sterilizing process is preferably of the peracetic/peroxy type. More preferably the sterilant is of the peracetic/peroxy type with an anticorrosive agent added thereinto. A suitable concentrate formulation of for use with the present invention includes from about 0.004 wt. % to about 30 wt. % hydrogen peroxide; 0.0003 wt. % to less than 55 wt. % peracetic acid; 0.025 wt. % to about 12 wt. % acetic acid; water; and an anticorrosive additive in an amount of from about 0.001 wt. % up to the solubility limit of the additive. Preferably, the additive may be sodium pentakis (2-ethyl hexyl) triphosphate and phosphoric acid; potassium perfluoroalkyl sulfonate; the sodium hydroxide reaction products of an aliphatic alcohol and phosphoous pentoxide; or combinations thereof.

Most preferably the additive is 20%–45% by weight mono sodium salt of phosphoric acid, mono (2-ethyl hexyl) ester; 20%–30% by weight pyrophosphonic acid, bi (2-ethyl hexyl) esters, sodium salts; 10%–25% by weight polyphosphonic acids, (2-ethyl hexyl) esters; less than 10% by weight phosphoric acid, bis (2-ethyl hexyl) ester, sodium salt; less than 3% by weight 2-ethyl hexanol; less than 5% by weight phosphoric acid, mono and di sodium salts; and 20%–25% by weight water.

A suitable use dilution formulation for use with the catheter reprocessing system in accordance with the present invention is from about 18 wt. % to about 30 wt. % hydrogen peroxide; from about 3 wt. % to about 5 wt. % peracetic acid; from about 6 wt. % to about 10 wt. % acetic acid; from about 0.001 wt. % up to the solubility limit of the anti-corrosive additive described above.

2. Circulate Sterilant. Valves V1, V4, V5, V6, V7, V11 and V13 are open. Sterilant is pumped from tank 382 through valves V1 and V11. A temperature sensor in tank 382 provides an electronic signal to heater 380 to maintain the temperature of sterilant pumped through the heater 380 at a constant at 38° C. Sterilant is pumped through valves V13 and V6 through the guidewire lumen fill and drain valve 158 and into the guidewire lumen inlet port 22. Sterilant exits the guidewire lumen (not shown) through guidewire lumen outlet port 26 and flows into cassette 34. Sterilant also flows from valves V13 through V5 into the central duct 168 of recirculating fill and drain valve 154 and exits through jet aperture 190 into the interior of cassette 34. Sterilant again flows through the overflow vent outlet 194, overflow vent 192 and overflow valve 156, through valve V7 and into tank 382. Valve V4 is open to provide monitoring of the pressure within the manifold 62 by transducer 374.

Every 120 seconds during the Circulate Sterilant step, the microprocessor checks pressure by the method described in step 1 above. If pressure exceeds 8 psi, the system is vented until the pressure in the system returns to 6 psi.

3. Test Guidewire Lumen for Blockages.

Part A—Pressurize Guidewire Lumen. Valves V1, V4, V6, V7, V11 and V13 are open. The guidewire lumen (not shown) is pressurized to 2 Barr for five seconds by pump 378. This process flushes the guidewire lumen (not shown) with sterilant that flows from tank 382 through Valves V1, V11, heater, V13, and V6, into guidewire lumen fill and drain valve 158, through guidewire lumen inlet port 22 and exits through guidewire lumen outlet port 26 into cassette 34. Excess sterilant is vented through overflow vent outlet 194, overflow vent 192 and overflow valve 156 and circulated back to tank 382. Valve V4 is open to provide monitoring of the pressure within the guidewire lumen (not shown) by the transducer 374.

Part B—Monitor Pressure. The pump 380 and all valves except valves V4, V6 and V7 are closed. The pressure previously created in Part A of Step 3 above is monitored for five seconds. A drop in pressure indicates an open lumen. Pressure which is maintained constant indicates a blockage in the guidewire lumen (not shown). If a blockage is detected, monitor 38 will indicate an error in reprocessing and signal that the guidewire lumen (not shown) is blocked. The reprocessing cycle will automatically stop. The cassette 34 remains full to indicate to the operator that the catheter 10 has failed. The operator must enter "clear" on the control panel 54 to drain tank 382 (see Step 13 below) and to restart the main menu. If no blockages are found, the reprocessing and sterilizing process will automatically continue.

4. Test Integrity of Balloon.

Part A—Inflate Balloon. Valves V1, V4, V11 and V13 are open. Pump 380 is turned on by the microprocessor. Balloon 14 is inflated to its maximum operating pressure, typically 6 Barr, by sterilant flowing from tank 382, through valves V1, V11, V13, V4 into first balloon inflation fill and drain valve 160, balloon inflation lumen inlet port 20, balloon inflation lumen and balloon 14. The pressure at which inflation of the balloon 14 is maintained will vary depending on the manufacture of the particular balloon-tipped catheter being reprocessed.

Part B—Monitor Pressure. All valves are closed. Pump 380 is turned off leaving the balloon 14 under pressure for approximately seven seconds. The pressure transducer 374 is monitored by the microprocessor for a drop in pressure which would indicate a leak or a failed balloon 14. If the balloon 14 fails, the monitor 38 will indicate an error in reprocessing and signal that balloon 14 has failed. Operator must enter "clear" on control 54 to drain tank 382 (see Step 13 below) and to restart the main menu. If the integrity of balloon member 14 is intact, the reprocessing and sterilizing process will automatically continue.

5. Circulate Sterilant at 53° C. Valves V1, V4, V5, V6, V7, V11 and V13 are open. Once valves are open, pressure inside the balloon 14 forces sterilant to exit out of the balloon inflation lumen, through balloon inflation inlet port 20, first balloon inflation fill and drain valve 160, through valves V4 and V5 and into cassette 34.

Concurrently, sterilant is pumped from tank 382 through valves V1 and V11. A temperature sensor in tank 382 provides an electronic signal to heater 380 to maintain the temperature of the sterilant constant at 53° C. as the sterilant is pumped through heater 380. Sterilant is pumped through valves V13 and V6 through the guidewire lumen fill and drain valve 158 into guidewire lumen inlet port 22 and guidewire lumen (not shown) and exits out guidewire outlet port 26. Sterilant again flows through the overflow vent outlet 194, overflow vent 192 and overflow valve 156, through V7 and into tank 382. Valve V4 is open to provide monitoring of the pressure within the manifold 62 by transducer 374. An internal timing device (not shown) is triggered which tracks the exposure time of the catheter at 53° C. and stores the information in the catheter data base in computer 36.

6. Clear Balloon Inflation Connecting Channel. Valves V1, V4, V8, V11 and V13 are open. Sterilant is pumped from the tank 382 through valves V1, V11, heater 380, valves V13 and V4, into first balloon inflation lumen fill and drain valve 160, through U-shaped connecting channel 164 and out through second balloon inflation lumen fill and drain valve 162 through valve V8 and circulated back to the tank 382. Fresh sterilant is now positioned at balloon inflation valve outlet port 202 at the entrance to balloon inflation line 204. This step ensures that fresh sterilant will be delivered to the interior of balloon during the inflation and deflation steps.

7. Sterilize Balloon.

Part A—Inflate Balloon. Valves V1, V4, V7, V11 and V13 are open. The pump 378 is turned on by the microprocessor. Balloon 14 is inflated to approximately 3 Barr by sterilant flowing from the tank 382, through valves V1, V11, V13, V4 into first balloon inflation fill and drain valve 160, balloon inflation lumen inlet port 20 and balloon 14. A pump drive circuit (not shown) receives electronic signals from pressure transducer 374 mounted on manifold 62 which allows the pump drive circuit to control the amount of pressure applied to balloon 14. Valve V7 is open to equalize pressure between cassette 34 and tank 382.

Part B—Deflate Balloon, Valves V1, V4, V7, V10 and V12 are open. Balloon 14 is evacuated to about 300 mm Hg by pump 378. Sterilant exits balloon 14 through balloon inflation lumen, through balloon inflation lumen inlet port 20 into first balloon inflation fill and drain valve 160 into valves V4, V10, pump 378, heater 380, valves V12 and V1, and back into tank 382. Valve V7 is open to equalize pressure between cassette 34 and tank 382.

In the preferred embodiment, balloon 14 is inflated and deflated a total of 20 times to ensure that the balloon 14 has been adequately flushed with sterilant. After every inflate and deflate cycle, the system pressure is checked as described in Step 1 above. If pressure exceeds 8 psi, the system is vented until the pressure in the system returns to a pressure of 6 psi. After every five inflate and deflate sequences, sterilant is circulated until the temperature of the sterilant once again reaches 53° C.

8. Circulate Sterilant at 53° C. Valves V1, V4, V5, V6, V7, V11 and V13 are open. Sterilant is pumped from tank 382 through valves V1 and V11. A temperature sensor in tank 382 provides an electronic signal to heater 380, to maintain the temperature of sterilant constant at 53° C. as sterilant is pumped through coils 388 of heater 380. Sterilant is pumped through valves V13 and V6 through the guidewire lumen fill and drain valve 158 into the guidewire lumen inlet port 22 and exits out guidewire lumen outlet port 26 into cassette 34. Sterilant again flows through the overflow vent outlet 194, overflow vent 192 and overflow valve 156, through valve V7 and into tank 382. Valve V4 is open to monitor pressure transducer 374 to avoid over pressurizing. Sterilant is circulated in this manner for the balance of the exposure time, or approximately 30 minutes.

9. Test Guidewire Lumen

Part A—Pressurize Guidewire Lumen. Valves V1, V4, V6, V7, V11 and V13 are open. The guidewire lumen (not shown) is pressurized to 2 Barr for five seconds by pump 378. This process flushes the guidewire lumen (not shown) with sterilant that flows from tank 382 through valves V1, V11, heater 380, valves V13 and V6, into guidewire lumen fill and drain valve 158, guidewire lumen inlet port 22, guidewire lumen (not shown), guidewire lumen outlet port 26 and into cassette 34. Excess sterilant is vented through overflow vent outlet 194, overflow vent 192 and overflow valve 156 and circulated back to tank 382. V4 is again open to monitor pressure.

Part B—Monitor Pressure. The pump 378 and all valves except V4, V6 and V7 are closed. Pressure previously created in step A above is monitored for five seconds. A drop in pressure indicates an open lumen. Pressure which is maintained indicates a blockage in guidewire lumen (not shown). If a blockage is detected, monitor will indicate an error in reprocessing and signal that the guidewire lumen (not shown) is blocked. The reprocessing cycle will automatically stop; the operator must enter clear to drain the tank 382 and to restart the main menu. If a blockage is not detected, the reprocessing cycle continues.

10. Drain Cassette to Tank 382. Valves V1, V5, V7, V10 and V12 are open. Cassette 34 is drained by sterilant flowing out jet aperture 190, recirculating fill and drain valve 154 to valve V10, pump 378, heater 380, through valves V12 and V1 and into tank 382. Valve V7 is open to equalize pressure between the cassette 34 and tank 382. After the cassette 34 is drained, the monitor 38 will prompt the operator to place the cap 144 on cassette 34 and press the fill cap key. The cassette 34 remains under pressure.

11. Fill Cap. Valves V1, V4, V5, V8, V11 and V13 are open. Sterilant flows from tank 382 through valves V1 and V11, pump 378, heater 380, valves V13 and V5, into purge-in port 326, through first duck bill valve 334, first fluid flow channel 316, interior chamber 320 and out through second fluid flow channel 318, second duck bill valve 336, purge-out port 328, through valves V8 and into tank 382. Valve V4 is open to monitor the pressure within the cap 144 by transducer 374. The pressure in the cassette is now preferably equal to 4–5 psi. Traces of sterilant remain in the fluid flow channels 316, 318 and the interior chamber 320.

The entire reprocessing and sterilizing process takes less than one hour. The cassette 34 is now ready to be stored for periods of one week to one month and rinsed later or may be rinsed immediately. If the cassette 34 is to be stored, the operator removes it from the dock 58. After the reprocessing cycle is completed, cap 144 is placed on cassette 34. The cap 144 functions to maintain the sterility of the catheter 10 by exposing the mouth 170 and the first end 178 of plunger 174 of valves 154–162 to a constant supply of sterilant. Cap 144 also prevents an operator from accidently coming into contact with the retractable plunger 174 thereby exposing the now sterile catheter to contaminated air.

Indentation 33 in cap 144 allows the operator easy access to the cam lever and knob assembly 226 of locking mechanism 152 to unlock the cassette to remove catheter 10 at the appropriate future time.

12. Rinsing. The catheter may be rinsed as disclosed in U.S. Pat. No. 4,721,123 or may be rinsed manually by the operator immediately prior to use. If rinsed manually, the operator must verify that the cassette is pressurized by pressing on the pressure monitor. The monitor will return to the extended position when released if the pressure has been maintained. Holding the cassette 34 upright, the operator releases the pressure by slowly moving the cam lever and knob assembly downwardly towards its open position. The catheter 10 is disconnected from luer lock connectors 206 and removed from tray 140.

The catheter 10 is immersed in sterile saline. The balloon inflation lumen and the guidewire lumens are flushed and aspirated by injecting four syringes containing approximately 5–10 cc of sterile saline thereinto. The aspirated sterile saline is tested with a residual test strip designed to measure the level of residual sterilant. When the test strip indicates that less than 3 ppm of hydrogen peroxide is present, the catheter is ready for re-use.

13. Drain Tank. Valves V1, V3, V9, V11, and V13 are open. Sterilant empties from tank 382, through valves V1, V11, pump 378, valves V13 and V13 and into a convenient disposal container. Valve V9 is open to allow air to replace the sterilant draining from the tank 382.

Although the description of the preferred embodiment has been presented, it is contemplated that various changes, including those mentioned above, could be made without deviating from the spirit of the present invention. It is therefore desired that the present embodiment be considered in all respects as illustrative, not restrictive, and that reference be made to the appended claims rather than to the foregoing description to indicate the scope of the invention.

We claim:

1. A method for reprocessing and sterilizing a previously used catheter comprising the steps of:
   (a) providing a catheter receiving housing and a catheter, having at least one lumen and a balloon member;

(b) enclosing said catheter within said catheter receiving housing;

(c) heating an external source of a sterilant to a temperature of about 53° C.;

(d) introducing said sterilant into said catheter receiving housing;

(e) causing said sterilant to circulate throughout said catheter receiving housing and around and within said catheter, said at least one lumen and said balloon member while constantly maintaining said temperature of about 53° C.;

(f) draining said sterilant from said catheter receiving housing;

(g) pressurizing said catheter receiving housing to a pressure level above said ambient pressure;

(h) maintaining said pressure level within said catheter receiving housing whereby the sterility of said catheter is maintained in a dry, sterile environment for at least one week by retaining said catheter in said pressurized catheter receiving housing.

2. The method as received in claim 1 wherein introducing sterilant into said catheter receiving housing further includes the step of:

(a) providing an anti-corrosive sterilant within said catheter receiving housing and within said catheter, said anti-corrosive sterilant comprising a mixture of hydrogen peroxide, peracetic acid, acetic acid, an anticorrosive agent and water.

3. The method as received in claim 1 wherein circulating said heated sterilant throughout said catheter receiving housing, said at least one lumen, and said balloon member further includes the step of:

(a) testing said at least one lumen for blockages by pressurizing said at least one lumen and monitoring said at least one lumen for a drop in pressure.

4. The method as recited in claim 3 wherein the step of testing said at least one lumen is repeated a plurality of times.

5. The method as received in claim 1 wherein the step of maintaining the pressure within said catheter receiving housing further includes the step of:

(a) providing a sterility maintaining cap means to said catheter receiving housing for ensuring that the sterility of said catheter having at least one lumen and a balloon member is maintained during storage.

6. The method as received in claim 1 wherein causing said sterilant to circulate within said catheter receiving housing, said at least one lumen and said balloon member further includes the step of:

(a) testing the integrity of said balloon member by inflating said balloon member with said sterilant under pressure and monitoring said balloon member for a drop in pressure; and (b) sterilizing said balloon member within about 30 minutes by inflating and deflating said balloon member with said sterilant.

7. The method as recited in claim 1 further including the step of sterilizing said catheter in less than about one hour.

8. An apparatus for selectively coupling a previously used catheter to a source of sterilant for reprocessing and sterilizing said catheter, and for storing said catheter in a sterile environment for at least one week, said apparatus comprising:

(a) housing means for receiving a catheter, said housing means including sidewalls defining a catheter receiving chamber having a mouth portion, said mouth portion having an outer perimeter for permitting access to said catheter receiving chamber, and latch means coupled to said sidewalls;

(b) removable door means detachably coupled to said housing means for selectively enclosing a catheter having at least one lumen within said catheter receiving chamber;

(c) a plurality of valves operably carried by said removable door means for selectively coupling said housing means to a source of sterilant;

(d) sealing means operably engageable with said removable door means and said plurality of valves for selectively maintaining pressure within said housing means for at least one week when said housing means is removed from said source of sterilant; and (e) a sterility maintaining cap detachably engageable with said plurality of valves and said door means, said sterility maintaining cap defining a plurality of interior valve receiving pockets and an interior channel extending substantially the length of said sterility maintaining cap, said interior channel being in fluid communication with each of said plurality of interior valve receiving pockets.

9. The apparatus as recited in claim 8, wherein said removable door means comprises:

(a) a door; and (b) locking means operably coupled to said door.

10. The apparatus as recited in claim 9, wherein said locking means comprises:

(a) an overcenter cam mechanism, said overcenter cam mechanism including at least two journals coupled to said door, said at least two journals each defining a peg receiving aperture;

(b) a cam shaft including at least two pegs, said at least two pegs rotatably received within said at least two journals, and said cam shaft shiftable between a locked and an unlocked position; and (c) a finger operable lever assembly coupled to said cam shaft for shifting said cam shaft between said locked and unlocked positions.

11. The apparatus as recited in claim 8, wherein said sealing means comprises latch means operably coupled to said housing means for detachably sealing said removable door means to said housing means; and an O-ring, said O-ring detachably received within a groove defined by the perimeter of said mouth portion.

12. The apparatus as recited in claim 11 wherein said latch means includes a plurality of latches, each latch having an arm defining at least one recessed notch.

13. The apparatus as recited in claim 8, wherein said housing means includes sterility monitoring means for monitoring the sterility of the reprocessed catheter during said storage.

14. The apparatus as recited in claim 8, wherein said sterility maintaining cap further includes a plurality of purge-in and purge-out ports operably connected to said plurality of interior valve receiving pockets, said plurality of purge-in and purge-out ports being in fluid communication with said plurality of interior valve receiving pockets and said interior channel.

* * * * *

UNITED STATES PATENT AND TRADEMARK OFFICE
CERTIFICATE OF CORRECTION

PATENT NO. : 5,310,524
DATED : May 10, 1994
INVENTOR(S) : Campbell et al.

It is certified that error appears in the above-indentified patent and that said Letters Patent is hereby corrected as shown below:

Column 7, line 28, delete "26" substitute --206-- therefor

Column 7, line 33, insert --,-- between 208 and 210 (i.e. 208,210)

Column 8, line 14, delete "ill" substitute --fill-- therefor

Column 9, line 55, delete "?42" substitute --342-- therefor

Column 17, line 21, delete "received" substitute --recited-- therefor

Column 17, line 29, delete "received" substitute --recited-- therefor

Column 17, line 40, delete "received" substitute --recited-- therefor

Column 17, line 47, delete "received" substitute --recited-- therefor

Signed and Sealed this

Fourteenth Day of March, 1995

Attest:

BRUCE LEHMAN

*Attesting Officer*     *Commissioner of Patents and Trademarks*